US00PP35423P2

(12) United States Plant Patent
Hoogendoorn

(10) Patent No.: US PP35,423 P2
(45) Date of Patent: Oct. 17, 2023

(54) ***HYDRANGEA* PLANT NAMED 'PERLA59361'**

(50) Latin Name: *Hydrangea macrophylla*
Varietal Denomination: Perla59361

(71) Applicant: Cornelis Hoogendoorn, Zevenhuizen (NL)

(72) Inventor: Cornelis Hoogendoorn, Zevenhuizen (NL)

(73) Assignee: PERLANOVA BREEDING VOF, Zevenhuizen (NL)

( * ) Notice: Subject to any disclaimer, the term of this patent is extended or adjusted under 35 U.S.C. 154(b) by 0 days.

(21) Appl. No.: 18/094,297

(22) Filed: Jan. 6, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla* plant named 'Perla59361' that is characterized by its compact plant habit, its terminal and axillary inflorescences, its inflorescences with sterile sepals that are deep red-pink in color with white margins, its early flowering, and its high resilience in warm and sunny growing conditions.

2 Drawing Sheets

Botanical classification: *Hydrangea macrophylla.*
Varietal denomination: 'Perla59361'.

BACKGROUND OF THE INVENTION

The present invention relates to a new and distinct cultivar of *Hydrangea macrophylla* and will be referred to hereafter by its cultivar name, 'Perla59361'. 'Perla59361' represents a new mophead type *Hydrangea*, a deciduous shrub grown for use as a landscape plant.

'Perla59361' was derived from an ongoing breeding program conducted by the Inventor in Zevenhuizen, The Netherlands. A goal of the breeding program was to develop new cultivars of *Hydrangea macrophylla* that flower on first year wood and are resilient in warm and sunny climates.

The Inventor made a controlled cross in June of 2015 in Zevenhuizen, The Netherlands between unnamed and unpatented proprietary plants from their breeding program; female parent (ref code 13-01) and male parent (ref code 15-26-57-01). 'Perla59361' was selected in June of 2018 as a single unique plant amongst the resulting seedlings.

Asexual propagation of the new cultivar was first accomplished under the direction of the Inventors by stem cuttings in May of 2019 in Zevenhuizen, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Perla59361' as a unique cultivar of *Hydrangea.*

1. 'Perla59361' exhibits a compact plant habit.
2. 'Perla59361' exhibits terminal and axillary inflorescences.
3. 'Perla59361' exhibits inflorescences with sterile sepals that are deep red-pink in color with white margins.

4. 'Perla59361' exhibits flowering early in the growing season.
5. 'Perla59361' exhibits high resilience to warm and sunny growing conditions.

The female parent of 'Perla59361' differs from 'Perla59361' in having sterile flower sepals that are all pink in color, fewer lateral branches, longer lateral branches, and a later blooming period. The male parent of 'Perla59361' differs from 'Perla59361' in having sterile flower sepals that are light pink in color with broader white margins, more lateral branches, and a much lower tolerance to warm and sunny climates. 'Perla59361' can be most closely compared to the *Hydrangea macrophylla* cultivars 'Saxcanhea' (not patented) and 'Bavaria' (not patented). Both 'Saxcanhea' and 'Bavaria' are similar to 'Perla59361' in having bi-color flowers. 'Saxcanhea' and 'Bavaria' both differ from 'Perla59361' in having different color sterile flower sepals. 'Saxcanhea' is light pink in color with broader white margins and 'Bavaria' is lavender blue with broader white margins. Both have more lateral branches and lower tolerance to warm and sunny growing conditions.

BRIEF DESCRIPTION OF THE DRAWINGS

The accompanying color photographs illustrates the overall appearance and distinct characteristics of the new *Hydrangea*. The photographs were taken of a 4-year-old plant as grown in a greenhouse in a 15-cm container in Zevenhuizen, The Netherlands.

The photograph in FIG. 1 provides a side view of the plant habit of 'Perla59361' in bloom.

Figure 1:
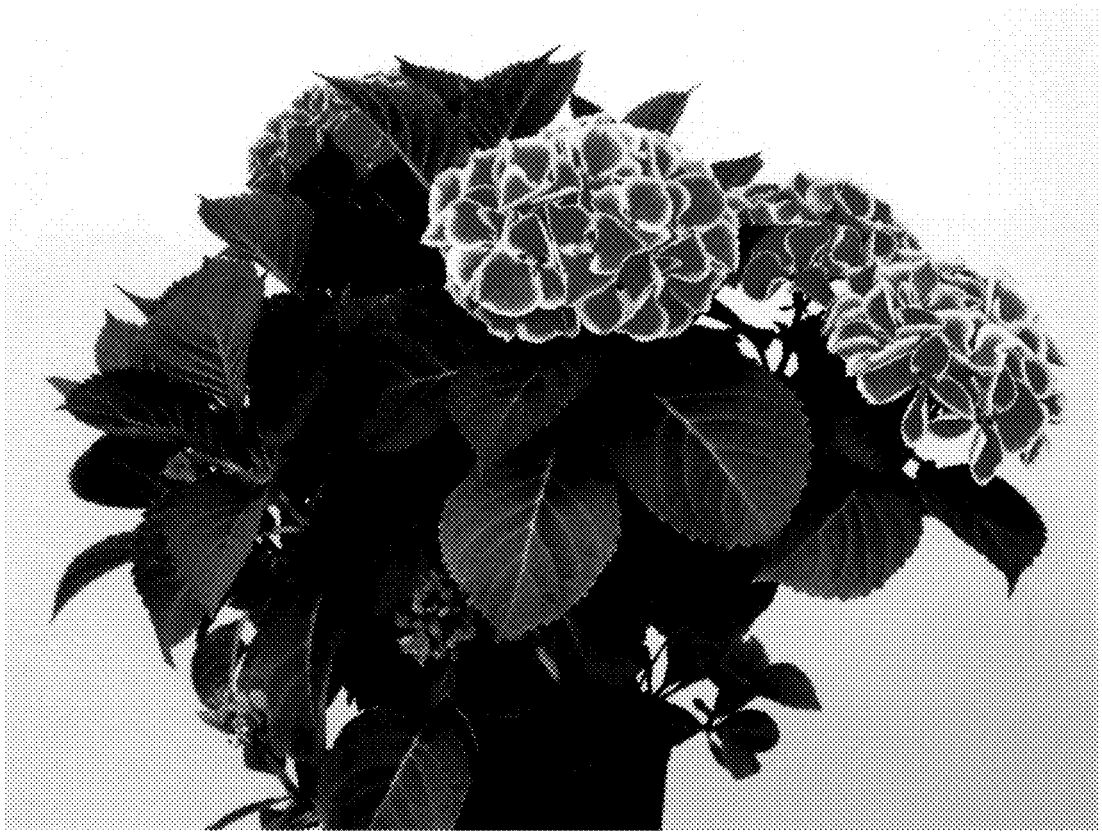
Figure 2:
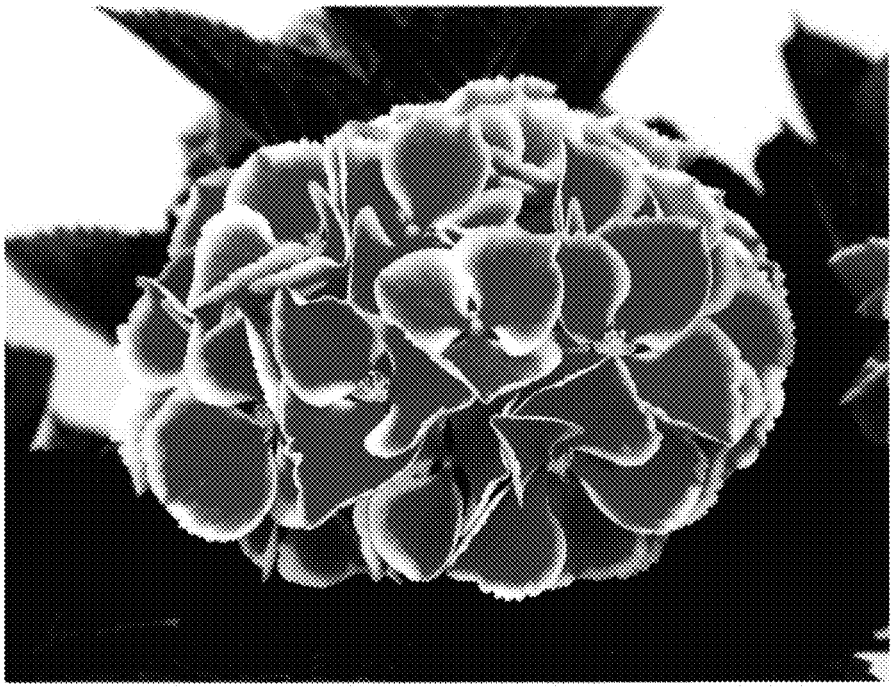

The photograph in FIG. 2 provides a close-up view of an inflorescence of 'Perla59361'.

Figure 3:
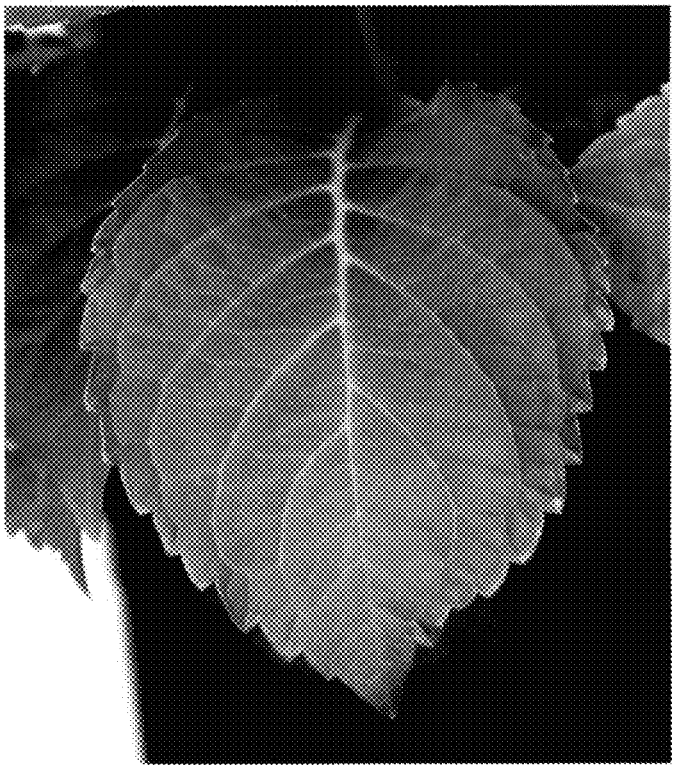

The photograph in FIG. 3 provides a close-up view of a leaf of 'Perla59361'.

The colors in the photographs may differ slightly from the color values cited in the detailed botanical description, which accurately describe the colors of the new *Hydrangea.*

BOTANICAL DESCRIPTION OF THE PLANT

The following is a detailed description of 4-year-old plants of 'Perla59361' as grown in a greenhouse in 15-cm containers in Zevenhuizen, The Netherlands. The plants were grown under non-blueing conditions and blueing conditions have not been used. The color determination is in accordance with The 2015 Colour Chart of The Royal Horticultural Society, London, England, except where general color terms of ordinary dictionary significance are used.

General description:

*Blooming period.*—April to October in The Netherlands.

*Plant type.*—Deciduous shrub, mophead type *Hydrangea.*

*Plant habit.*—Compact, suitable for container growing.

*Height and spread.*—Average of 42 cm in height, 70 cm in spread.

*Hardiness.*—U.S.D.A. Zones 5 to 7.

*Diseases and pests.*—No resistance or susceptibility to diseases or pests has been observed.

*Root description.*—Fine and fibrous.

*Propagation.*—Softwood stem cuttings.

*Growth rate.*—Vigorous.

*Root development.*—Time required for root initiation is 4 to 5 weeks, time required to produce a young plant from rooted cutting is an average of 6 months.

Stem description:

*Stem shape.*—Rounded.

*Stem strength.*—Strong.

*Stem color.*—Young; 144A in color, mature; 146D, internodes a blend of N186B and N186C, older bark; 199B to 199D.

*Stem size.*—An average of 23.3 cm in length, 6 mm in diameter.

*Stem surface.*—Younger and mature stems; glabrous, lenticellate, lenticles; very sparse 5 per $cm^2$, an average of 1.5 mm in length and 0.5 mm in width, N186B in color, old growth at base; bark-like, mostly smooth and can be slightly exfoliating.

*Stem aspect.*—Average angle of 45°, varying between 20° and 90°.

*Internode length.*—Average of 4.6 cm.

*Branching.*—An average of 20 lateral branches per plant.

Foliage description:

*Leaf shape.*—Broadly elliptic to broadly obovate.

*Leaf arrangement.*—Opposite.

*Leaf division.*—Simple.

*Leaf base.*—Short attenuate, obtuse to very shallow truncate.

*Leaf apex.*—Broadly apiculate.

*Leaf margins.*—Coarsely dentate-serrate.

*Leaf venation.*—Pinnate, upper surface color; 145A, lower surface color; 145B.

*Leaf size.*—Average of 12.6 cm in length and 9.6 cm in width.

*Leaf attachment.*—Petiolate.

*Leaf surface.*—Both surfaces smooth and slightly rugose, tufts of very short hairs are present in the vein axils on leaf-undersides, average length of hairs 0.5 mm, too small to measure color.

*Leaf color.*—Young upper surface 137A, young lower surface; 146B, mature upper surface NN137B, mature lower surface; 147B.

*Petioles.*—An average of 2.2 cm in length and 4 mm in diameter, both surfaces slightly glossy and smooth, 145A in color.

Inflorescence description:

*Inflorescence type.*—Terminal panicle, mophead in form, comprised of single sterile flowers and fertile flowers.

*Lastingness of inflorescence.*—Sterile flowers; 6 weeks, persistent, fertile flowers; 3 days, self-cleaning.

*Inflorescence number.*—One per lateral.

*Inflorescence size.*—Average of 10.3 cm in height, 17.7 cm in diameter.

*Flower number.*—Average of 60 sterile flowers and 52 fertile flowers per panicle.

*Flower aspect.*—Sterile flowers; upright to outward, fertile flowers; upright.

*Flower size.*—Sterile flowers; an average of 6.3 cm in diameter, 2.2 cm in depth, fertile flowers; an average of 1.2 cm in diameter and 7 mm in depth.

*Flower type.*—Rotate.

*Flower buds.*—Sterile flowers; average of 1.4 cm in length, 1.9 cm in diameter, irregularly broadly cup-shaped, color; 145B, tip 51B, fertile flowers; 4 mm in length, 4.5 mm in diameter, flattened broadly ovate in shape, color; 54B, immature calyx 150B.

*Peduncles.*—Strong, average of 3.6 cm in length and 3.5 mm in width, color; 144C, very strongly tinged at nodes with N186B to N186C, angle varies between vertical and 40°, surface is slightly glossy to matte, very sparsely covered with short soft hairs, an average of 1 mm in length, too small to measure color.

*Pedicels.*—Sterile flowers; moderately strong, average of 2.9 cm in length and 1.5 mm in diameter, average angle of 35°, color; 63C, base 63D, surface is matte and densely covered with very short hairs, average of 0.3 mm in length, too small to measure color, fertile flowers; moderately strong, average of 4 mm in length and 1 mm in diameter, average angle of 20°, color; 181C, surface is very slightly glossy, glabrous.

*Petals.*—Sterile flowers; 4, rotate, 5 mm in length, 3 mm in diameter, ovate to concave in shape, acute apex, cuneate base, entire margins, glabrous, smooth, matte surface, color; when opening and fully open upper surface; 64C, base and margins 69D, when opening and fully open lower surface; 63B, base and margins 69D, fertile flowers; 4 to 5, rotate, 5 mm in length, 3 mm in diameter, ovate to concave in shape, acute apex, cuneate base, entire margins, glabrous and matte surface, color; when opening and fully open upper surface 64C, base and margins 69D, when opening and fully open lower surface 63B, base and margins 69D.

*Sepals.*—Sterile flowers; 4, occasionally 3 or 5, reniform, moderately concave in shape, strongly overlapping, rotate, cruciform in arrangement, margins coarsely dentate-crenate, very slightly coarsely undulate, apex is broadly bluntly acute to nearly obtuse, cuneate base, average of 3.3 cm in length and 4 cm in width, upper and lower surface glabrous and matte, color; when opening upper surface 53C, base 53D, margins 150C, color; when opening lower surface 54B, margins 150C, when fully open upper surface a blend of 53C and 63A, margins N155B, fading to 178B, base 184C, margins 150A, when fully open lower surface 54B and 63B, margins, fading to 182C, tinged N148B, margins 150A, fertile flowers; 5, rotate in arrangement, broadly ovate to deltoid in shape, entire margins, acute apex, cuneate base, average of 0.1 mm in length and width, both surfaces are glabrous and matte, color; when opening upper and lower surface 150C, when fully open upper surface 150C, when full open lower surface 150C, tinged 55C.

Reproductive organs:

*Stamens.*—Sterile flowers; stamens; average of 8, anthers; broad oblong in shape, 1.25 mm in length and 157D in color, filaments; 4 mm in length, 65D in color, pollen; moderate in quantity, 155A in color, fertile flowers; stamens; average of 10, anthers; broadly oblong in shape, 1.25 mm in length and 157D in color, filament is 4 mm in length and 155A in color, pollen is moderate in quantity, 155A in color.

*Pistils.*—Sterile flowers; pistils; average of 2, an average of 1.75 mm in length, stigma; club-shaped, 0.75 in length and N155B in color, style; 54D in color, 1 mm in length, ovary; 155A in color, fertile flowers; pistils; 2 to 3, an average of 2.5 mm in length, stigma; club-shaped, NN155A in color, style; 1.5 mm in length, 69C to 69D in color, ovary; 69C to 69D.

*Fruit and seed.*—Not observed to date.

It is claimed:

1. A new and distinct cultivar of *Hydrangea* plant named 'Perla59361' substantially as herein illustrated and described.

* * * * *